US012673015B2

(12) United States Patent
Hiban et al.

(10) Patent No.: US 12,673,015 B2
(45) **Date of Patent: \*Jul. 7, 2026**

(54) LOW SULFATE SURFACTANT COMPOSITION

(71) Applicant: Conopco, Inc., Englewood Cliffs, NJ (US)

(72) Inventors: Douglas John Hiban, Newtown, CT (US); Teanoosh Moaddel, Watertown, CT (US); Daniel Filipe Pereira, Naugatuck, CT (US); Tirucherai Varahan Vasudevan, Bethany, CT (US)

(73) Assignee: Conopco, Inc., Hoboken, NJ (US)

( * ) Notice: Subject to any disclaimer, the term of this patent is extended or adjusted under 35 U.S.C. 154(b) by 645 days.

This patent is subject to a terminal disclaimer.

(21) Appl. No.: 17/793,985

(22) PCT Filed: Jan. 20, 2021

(86) PCT No.: PCT/EP2021/051123
§ 371 (c)(1),
(2) Date: Jul. 20, 2022

(87) PCT Pub. No.: WO2021/148427
PCT Pub. Date: Jul. 29, 2021

(65) Prior Publication Data
US 2023/0049117 A1 Feb. 16, 2023

Related U.S. Application Data

(63) Continuation of application No. 16/748,521, filed on Jan. 21, 2020, now abandoned.

(30) Foreign Application Priority Data

Apr. 7, 2020 (EP) .................................... 20168571

(51) Int. Cl.
| | |
|---|---|
| *A61K 8/362* | (2006.01) |
| *A61K 8/34* | (2006.01) |
| *A61K 8/36* | (2006.01) |
| *A61K 8/42* | (2006.01) |
| *A61K 8/44* | (2006.01) |
| *A61K 8/46* | (2006.01) |
| *A61Q 19/10* | (2006.01) |

(52) U.S. Cl.
CPC ............. *A61K 8/466* (2013.01); *A61K 8/342* (2013.01); *A61K 8/361* (2013.01); *A61K 8/362* (2013.01); *A61K 8/42* (2013.01); *A61K 8/44* (2013.01); *A61Q 19/10* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 3,472,840 A | 10/1969 | Stone et al. | |
| 3,962,418 A | 6/1976 | Birkofer | |
| 4,663,159 A | 5/1987 | Brode et al. | |
| 5,009,814 A | 4/1991 | Kelkenberg et al. | |
| 5,192,462 A * | 3/1993 | Gloor ...................... | C11D 1/74 |
| | | | 554/227 |
| 5,389,279 A | 2/1995 | Au et al. | |
| 5,393,466 A | 2/1995 | Ilardi et al. | |
| 5,407,919 A | 4/1995 | Brode et al. | |
| 5,415,810 A | 5/1995 | Lee | |
| 5,925,603 A | 7/1999 | Paul | |
| 6,117,628 A | 9/2000 | Eichorst et al. | |
| 6,117,828 A | 9/2000 | Puvvada et al. | |
| 8,440,605 B2 * | 5/2013 | Wise ................... | C11D 11/0094 |
| | | | 510/156 |
| 8,524,211 B1 | 9/2013 | Rafiee et al. | |
| 8,778,910 B2 | 7/2014 | Palla-Venkata et al. | |
| 8,794,474 B2 | 8/2014 | Mueller et al. | |
| 2008/0153730 A1 | 6/2008 | Tsaur | |
| 2008/0255247 A1 | 10/2008 | Sagalowicz et al. | |
| 2009/0062406 A1 | 3/2009 | Loeffler | |
| 2012/0149629 A1 | 6/2012 | Dahms et al. | |

(Continued)

FOREIGN PATENT DOCUMENTS

| | | |
|---|---|---|
| CN | 101360481 | 2/2006 |
| CN | 102459554 | 5/2012 |

(Continued)

OTHER PUBLICATIONS

Nanofibrillated cellulose surface modification and potential applications; 2014; 5-31; 292.
Sun et al.; Journal of Cosmetic Science; 2003; 559-568; 54.
Search Report & Written Opinion in EP20168571; 24-Sep. 2020.
Search Report and Written Opinion in PCTEP2021051124; Apr. 29, 2021.
Search Report and Written Opinion in PCTEP2021051123; Mar. 1, 2021.

(Continued)

*Primary Examiner* — Sahana S Kaup
*Assistant Examiner* — Ashlee E Wertz
(74) *Attorney, Agent, or Firm* — Edward A. Squillane, Jr.

(57) ABSTRACT

The invention is directed to a hydratable concentrated surfactant composition. The composition is pourable, easy to dilute, substantially free of sulfate and oil, comprises a $C_6$-$C_{14}$ acid, alcohol or both, an anionic surfactant comprising acyl isethionate and an amphoteric surfactant, zwitterionic surfactant or both. The composition is in lamellar phase and thickens and transforms to an isotropic phase upon dilution. The composition can be used as a concentrate in small volumes and diluted as used and needed or can be diluted with water in refill packaging to ensure a reduction in plastic waste.

9 Claims, No Drawings

(56)  References Cited

U.S. PATENT DOCUMENTS

| | | | |
|---|---|---|---|
| 2016/0000669 A1 | 1/2016 | Hinman et al. | |
| 2016/0167293 A1 | 6/2016 | Bush et al. | |
| 2016/0296442 A1 | 10/2016 | Aubrun et al. | |
| 2016/0310388 A1 | 10/2016 | Smith, III et al. | |
| 2017/0151146 A1* | 6/2017 | Scheunemann | A61K 8/365 |
| 2017/0304173 A1 | 10/2017 | Elder | |
| 2018/0098923 A1 | 4/2018 | Hutton, III | |
| 2018/0280270 A1 | 10/2018 | Rughani et al. | |
| 2019/0031258 A1 | 1/2019 | Soik et al. | |
| 2019/0038544 A1 | 2/2019 | Adamy et al. | |
| 2019/0060200 A1 | 2/2019 | Adamy et al. | |
| 2019/0077578 A1 | 3/2019 | Eungrasamee et al. | |
| 2019/0282480 A1* | 9/2019 | Su | A61K 8/442 |
| 2021/0220243 A1 | 7/2021 | Hiban et al. | |
| 2023/0045404 A1 | 2/2023 | Shimuta et al. | |

FOREIGN PATENT DOCUMENTS

| | | | | |
|---|---|---|---|---|
| CN | 105050571 | 11/2015 | | |
| CN | 108697607 | 10/2018 | | |
| DE | 102007040909 | 3/2009 | | |
| DE | 102017216244 | 3/2019 | | |
| EP | 0133345 | 2/1985 | | |
| EP | 2532343 | 12/2012 | | |
| EP | 2552391 | 3/2018 | | |
| FR | 3012962 | 11/2013 | | |
| FR | 3077492 | 8/2019 | | |
| GB | 2568148 | 4/2021 | | |
| WO | WO9220776 | 11/1992 | | |
| WO | WO2011117650 | 9/2011 | | |
| WO | WO2011120780 | 10/2011 | | |
| WO | WO2013150300 | 10/2013 | | |
| WO | WO-2018206215 A1 * | 11/2018 | | A61K 8/44 |
| WO | WO2019011521 | 1/2019 | | |
| WO | WO2020025275 | 2/2020 | | |
| WO | WO2020233972 | 11/2020 | | |
| WO | WO2021148428 | 7/2021 | | |
| WO | WO2022150812 | 7/2022 | | |
| WO | WO2022150813 | 7/2022 | | |
| WO | WO2022150814 | 7/2022 | | |
| WO | WO2022150815 | 7/2022 | | |
| WO | WO2023275298 | 1/2023 | | |

OTHER PUBLICATIONS

Written Opinion of the IPEA in PCT/EP/2021/051124; Dec. 20, 2021.

Can coconut oil prevent hair fall; Nov. 25, 2018; 1-6.

* cited by examiner

LOW SULFATE SURFACTANT COMPOSITION

FIELD OF THE INVENTION

The present invention is directed to a hydratable concentrated surfactant composition. The composition is pourable, substantially free of sulfate and oil, comprises a $C_6$-$C_{14}$ acid, alcohol or both, anionic surfactant and an amphoteric surfactant, zwitterionic surfactant or both. The composition is in lamellar phase, and unexpectedly, thickens and transforms to an isotropic phase upon dilution. The composition can be used as a concentrate in small volumes and diluted as used and needed or can be diluted with water in refill packaging to ensure a reduction in plastic waste.

BACKGROUND OF THE INVENTION

Liquid based cleansing compositions, such as shampoos and body washes, are common and enjoyed by many consumers. Such compositions typically have water as the predominant ingredient, and they are often sold in plastic bottles or tubes. The compositions are conventionally formulated to have a viscosity that is customary for consumer use and easy for evacuation from the package they are sold in.

It is often publicized that the world's oceans will soon have more plastic than fish. Given environmental concerns and the desire for consumers and conscious companies to do more for the planet, there is a strong desire to use less plastic when selling products, including consumer products. In view of this, efforts have been made to sell product in concentrate form, and therefore, ship product that comprises less water. The difficulty with concentrates is consumers often do not like adding additional water to the concentrate and further work, like stirring, to convert the concentrate into an end usable product. As to the hydrated product, common complaints include that the product is not homogeneous after adding water and/or of undesirable viscosity.

It is of increasing interest to develop a concentrate that is easy to pour and hydrate, results in a consumer product that is ready to use in under five (5) minutes and of very desirable characteristics, including viscosity. It is also desirable to develop a concentrate that is substantially free of sulfate and that is easy to use with a refill package to reduce plastic waste. This invention, therefore, is directed to a composition that comprises a $C_6$-$C_{14}$ acid, alcohol or both, anionic surfactant and an amphoteric surfactant, zwitterionic surfactant or both. The composition is in lamellar phase, and unexpectedly, thickens and transforms to an isotropic phase upon dilution. The composition can be used as a concentrate and diluted as needed or can be diluted with water in refill packaging to ensure a reduction in plastic waste.

Additional Information

Efforts have been disclosed for making wash compositions. In U.S. patent application publication 2019/031258 A1, rheofluidifying concentrated foaming compositions are described.

Even other efforts have been disclosed for making wash compositions. In U.S. patent application publication 2018/098923 A1, personal care compositions substantially free of sulfated surfactants are described.

Still other efforts have been disclosed for making wash compositions. In U.S. patent application 2019/282480 A1, self-thickening cleansing compositions with N-acyl acidic amino acids or salts thereof and an amphoteric surfactant are described.

None of the additional information describes surfactant containing compositions as described and claimed in the present application.

SUMMARY OF THE INVENTION

In a first aspect, the present invention is directed to a hydratable concentrated surfactant composition having a viscosity from 25 to 10,000 cps (preferably from 25 to 7,500 cps, more preferably, from 250 to 3,500 cps) wherein the composition thickens and increases in viscosity when diluted with water at a composition to water weight ratio from 1:1 to 1:10 (preferably 1:2 to 1:7, more preferably 1:3 to 1:6) to produce an end use composition having a viscosity from 1,000 to 20,000 cps (preferably 2,000 to 15,000 cps, most preferably, 3,000 to 12,000 cps).

In a second aspect, the present invention is directed to the hydratable concentrated surfactant composition of the first aspect of the invention wherein the composition transforms from lamellar to isotropic form (i.e., microstructure) upon dilution.

In a third aspect, the present invention is directed to the hydratable concentrated surfactant composition having a viscosity from 25 to 10,000 cps wherein the composition is suitable to be diluted with water at a composition to water weight ratio from 1:1 to 1:10 to produce an end use composition having a viscosity from 1,000 to 20,000 cps and further wherein the hydratable composition comprises:

a) an anionic surfactant comprising acyl isethionate;

b) an amphoteric and/or zwitterionic surfactant;

c) a $C_6$-$C_{14}$ acid or alcohol structuring agent; and d) from 30 to 85% by weight water, the end use composition having a viscosity that is greater than the hydratable concentrated surfactant composition.

In a fourth aspect, the invention is directed to an end use composition prepared by diluting at least one of the hydratable concentrated surfactant compositions of the first three aspects of the invention.

In a fifth aspect, the invention is directed to the use of the end use composition of the fourth aspect of the invention to cosmetically treat skin.

As used herein, "compositions" with no qualifier is meant to mean the hydratable composition and end use composition of this invention. Hydratable, as used herein, means add and/or add and absorb water (i.e., to dilute) even to a composition that has water such as a composition that is initially 30 to 85% by weight water. Skin, as used herein, is meant to include skin on the arms (including underarms), face, feet, neck, chest, hands, legs, buttocks and scalp (including hair). Hydratable concentrated surfactant composition ("hydratable composition") means a lamellar composition that increases in viscosity when water is added to the composition to thereby produce an isotropic end use composition suitable for topical application. The hydratable composition is one which is even suitable to have a viscosity from 500 to 1,500 cps. (1 Pa-s is equal to 1000 cps). Such end use composition is one suitable to be wiped or washed off, and preferably, washed off with water. The end use composition can be a home care cleaning composition but is preferably a shampoo, make-up wash, facial wash, hand wash or personal care liquid body wash. In an embodiment of the invention, the end use composition can have a viscosity from 6,000 to 12,000 cps when a body wash and from 2,000 to 5,000 cps when a hand wash. The end use composition may, optionally, comprise medicinal or therapeutic agents, but preferably, is a wash which is cosmetic and non-therapeutic. In one embodiment of the invention, the end use composition is a home care composition like a table top or toilet cleaning composition. In another embodiment, the end use composition is a shampoo composition. In still another embodiment, the end use composition is a personal wash composition, and therefore, a liquid body wash. As hereinafter described, the end use composition of the present invention may optionally comprise skin benefit ingredients added thereto such as emollients, vitamins and/or derivatives thereof, resorcinols, retinoic acid precursors, colorants, moisturizers, sunscreens, mixtures thereof or the like. The skin benefit ingredients (or agents) may be water or oil soluble. If used, oil soluble skin benefit agents typically make up to 1.5% by weight of the hydratable composition whereby water soluble skin benefit agents, when used, typically make up to 10% by weight of the hydratable composition of the present invention. The hydratable composition and end use composition typically have a pH from 4.5 to 10. Viscosity, unless noted otherwise, is taken with a Discovery HR-2 Rheometer using sand blasted plates with a 100 micron gap and a shear rate of 4-15 s$^{-1}$. Viscosity is measured at 25° C. Increase in viscosity means the hydratable composition of the present invention will have a starting viscosity that is lower than the final viscosity after water is added and the resulting end use composition is made. The end use composition is made by combining water and hydratable composition and mixing (with moderate shear like stirring, preferably shaking) the same to produce the end use composition having a higher viscosity than the hydratable concentrate it is made from. In another embodiment, the hydratable composition may be applied directly to, for example, a consumer and when water and shear are applied (like, for example, shearing with the hand and water from a sink or shower) the desired end use composition may be made. As used herein, "substantially free of sulfate" means less than 6.0% by weight of the end use composition, and "substantially free of oil" means less than 0.3% by weight of the end use composition. The term comprising is meant to encompass the terms consisting essentially of and consisting of. For the avoidance of doubt, and for illustration, the end use composition of this invention comprising surfactant, water and active is meant to include a composition consisting essentially of the same and a composition consisting of the same. All ranges defined are meant to include all ranges subsumed therein. Except in the operating comparative examples, or where otherwise explicitly indicated, all numbers in this description indicating amounts or ratios of materials or conditions and/or physical properties of materials and/or use are to be understood as modified by the word "about".

DETAILED DESCRIPTION OF THE PREFERRED EMBODIMENTS

As to the anionic surfactant, the same typically makes up from 0.05 to 30% by weight of the hydratable composition, including all ranges subsumed therein. In an embodiment of the invention, the anionic surfactant makes up from 0.5 to 25% by weight, and preferably, from to 0.8 to 20% by weight of the hydratable composition, including all ranges subsumed therein. Still in another embodiment, anionic surfactant makes up from 12 to 18% by weight of the hydratable composition, including all ranges subsumed therein. In another embodiment, the anionic surfactant is 15 to 100%, and preferably, from 30 to 85%, and most preferably, from 35 to 80% by weight acyl isethionate, based on total weight of anionic surfactant, and including all ranges subsumed therein. In still another embodiment, the acyl isethionate is used with an additional anionic surfactant which preferably includes an acyl taurate (defined to include an acyl $C_{1-4}$alkyl taurate, preferably an acyl methyl taurate) and/or glycinate. When anionic surfactant in addition to isethionate is used, in an often preferred embodiment the additional anionic surfactant is an acyl taurate which can typically make up from 40 to 85%, and preferably, from 50 to 82%, and most preferably, from 60 to 80%, by weight by weight of the total anionic surfactant in the hydratable composition.

As to the amphoteric and/or zwitterionic surfactant used in the hydratable composition, the same typically makes up from 0.1 to 45%, and preferably, from 0.5 to 35%, and most preferably, from 12 to 25% by weight of the hydratable composition, including all ranges subsumed therein.

To, for example, aid in hydratable composition structuring and hydration, structuring agent like $C_6$-$C_{14}$ acid and/or alcohol (i.e., derivative thereof) can preferably be used and typically make up from 0.1 to 16%, and preferably, from 1.8 to 12%, and most preferably, from 3 to 8% by weight of the hydratable composition, including all ranges subsumed therein. The preferred structuring agent is myristic acid, lauric acid and any alcohol derivatives thereof. The structuring agent may be selected from the group consisting of $C_6$-$C_{14}$ fatty acid, $C_6$-$C_{14}$ fatty alcohol, $C_6$-$C_{14}$ fatty amide and mixtures thereof and may make up from 0.1 to 16%, and preferably, from 1.8 to 12%, and most preferably, from 3 to 8% by weight of the hydratable composition, including all ranges subsumed therein.

Inorganic salt is an optional but often desired ingredient to aid in composition thickening. Typical salts may be used like NaCl, KCl, $MgCl_2$, $CaCl_2$, mixtures thereof or the like. Typically, the inorganic salt makes up from 0 to 15%, and preferably, from 1 to 12%, and most preferably, from 0.75 to 4.5% by weight of the hydratable composition, including all ranges subsumed therein.

Polymeric viscosity aids are an optional but often desired ingredient in the hydratable composition of the present invention. Preferred polymers are those generally classified as high molecular weight ethoxylated fatty acid esters. Illustrative examples include PEG 120 methyl glucose dioleate, PEG 18 glyceryloleate/cocoate, PEG 150 pentaerythritol tetrastearate, mixtures thereof or the like. The often preferred polymeric viscosity aid is PEG 150 pentaerythritol tetrastearate which is sold under the Versathix name by Croda. When used, such aids make up from 0.01 to 0.8%, and preferably, from 0.1 to 0.5%, and most preferably, from 0.15 to 0.3% by weight of the hydratable composition, including all ranges subsumed therein.

In another embodiment of the invention, less than 3.0% by weight sulfate is present in the end use composition of the present invention, preferably less than 1.0% by weight, and most preferably, no (0.0% by weight) sulfate. In the present invention, the hydratable composition should be formulated such that upon dilution, the desired component/ingredient levels (such as sulfate levels) in the end use composition are attained.

As to anionic surfactants suitable for use in the hydratable composition and end use composition of the present invention, the anionic surfactant used can include aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate. The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of at least 1.0, preferably less than 5, and most preferably 1 to 4, and M is a solubilizing cation such as sodium, potassium, ammonium or substituted ammonium.

The anionic may also include alkyl sulfosuccinates (including mono- and dialkyl, e.g., $C_6$-$C_{22}$ sulfosuccinates); alkyl and acyl taurates (often methyl taurates), alkyl and acyl sarcosinates, sulfoacetates, $C_8$-$C_{22}$ alkyl phosphates and phosphonates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

$$R^1O_2CCH_2CH(SO_3M)CO_2M;$$

and amide-MEA sulfosuccinates of the formula:

$$R^1CONHCH_2CH_2O_2CCH_2CH(SO_3M)CO_2M$$

wherein $R^1$ ranges from $C_8$-$C_{22}$ alkyl.

Sarcosinates are generally indicated by the formula:

$$R^2CON(CH_3)CH_2CO_2M, \text{ wherein } R^2 \text{ ranges from } C_8\text{-}C_{20} \text{ alkyl.}$$

Taurates are generally identified by formula:

$$R^3CONR^4CH_2CH_2SO_3M$$

wherein $R^3$ is a $C_8$-$C_{20}$ alkyl, $R^4$ is a $C_1$-$C_4$ alkyl.

M is a solubilizing cation as previously described.

The isethionates that may be used include $C_8$-$C_{18}$ acyl isethionates (including those which have a substituted head group such as a $C_{1-4}$alkyl substitution, preferably methyl substitution). These esters are prepared by a reaction between alkali metal isethionate with mixed aliphatic fatty acids having from 6 to 18 carbon atoms and an iodine value of less than 20. Often at least 75% of the mixed fatty acids have from 12 to 18 carbon atoms and up to 25% have from 6 to 10 carbon atoms.

The acyl isethionate used may be an alkoxylated isethionate such as is described in Ilardi et al., U.S. Pat. No. 5,393,466, entitled "Fatty Acid Esters of Polyalkoxylated isethonic acid; issued Feb. 28, 1995; hereby incorporated by reference. This compound has the general formula:

$$R^5C\text{—}O(O)\text{—}C(X)H\text{—}C(Y)H\text{—}(OCH_2\text{—}CH_2)_m\text{—}SO_3M$$

wherein $R^5$ is an alkyl group having 8 to 18 carbons, m is an integer from 1 to 4, X and Y are each independently hydrogen or an alkyl group having 1 to 4 carbons and M is a solubilizing cation as previously described.

In an embodiment of the invention, an anionic surfactant used is sodium lauroyl glycinate, sodium cocoyl glycinate, sodium lauroyl glutamate, sodium cocoyl glutamate, sodium lauroyl isethionate, sodium cocoyl isethionate, sodium methyl lauroyl taurate, sodium methyl cocoyl taurate or a mixture thereof. Such anionic surfactants are commercially available from suppliers like Galaxy Surfactants, Clariant, Sino Lion and Innospec. Sodium cocoyl isethionate, sodium methyl lauroyl taurate, sodium lauroyl glyconate, sodium methyl lauroyl isethionate or mixtures thereof are the preferred anionics suitable for use.

Amphoteric surfactants suitable for use in the invention (which depending on pH can be zwitterionic) include sodium acyl amphoacetates, sodium acyl amphopropionates, disodium acyl amphodiacetates and disodium acyl amphodipropionates where the acyl (i.e., alkanoyl group) can comprise a $C_7$-$C_{18}$ alkyl portion. Illustrative examples of the amphoteric surfactants suitable for use include sodium lauroamphoacetate, sodium cocoamphoacetate, sodium lauroamphoacetate, sodium cocoamphoacetate and mixtures thereof.

As to the zwitterionic surfactants that may be employed in the present invention, such surfactants include at least one acid group. Such an acid group may be a carboxylic or a sulphonic acid group. They often include quaternary nitrogen, and therefore, can be quaternary amino acids. They should generally include an alkyl or alkenyl group of 7 to 18 carbon atoms generally comply with an overall structural formula:

$$R^6\text{—}[\text{—}C(O)\text{—}NH(CH_2)_q\text{—}]_r\text{—}{}_N{}^+\text{—}(R^7\text{—})(R^8)A\text{—}B$$

where $R^7$ is alkyl or alkenyl of 7 to 18 carbon atoms; $R^7$ and $R^8$ are each independently alkyl, hydroxyalkyl or carboxyalkyl of 1 to 3 carbon atoms; q is 2 to 4; r is 0 to 1; A is alkylene of 1 to 3 carbon atoms optionally substituted with hydroxyl, and B is —$CO_2$— or —$SO_3$—.

Suitable zwitterionic surfactants for use in the present invention and within the above general formula include simple betaines of formula:

$$R^6\text{—}N^+(R^7)(R^8)CH_2CO_2^-$$

and amido betaines of formula:

$$R^6\text{—}CONH(CH_2)_t\text{—}N^-\text{—}(R^7)(R^8)CH_2CO_2^- \text{ where t is 2 or 3.}$$

In both formulae $R^6$, $R^7$ and $R^8$ are as defined previously. $R^6$ may, in particular, be a mixture of $C_{12}$ and $C_{14}$ alkyl groups derived from coconut oil so that at least half, preferably at least three quarters of the groups $R^6$ have 10 to 14 carbon atoms. $R^7$ and $R^8$ are preferably methyl.

A further possibility is that the zwitterionic surfactant is a sulphobetaine of formula:

$$R^6\text{—}N^-\text{—}(R^7)(R^8)(CH_2)_3SO_3$$

or $$R^6\text{—}CONH(CH_2)_u\text{—}N^-\text{—}(R^7)(R^8)(CH_2)_3SO_3^-$$

where u is 2 or 3, or variants of these in which —$(CH_2)_3SO_3^-$ is replaced by —$CH_2C(OH)(H)CH_2SO_3^-$.

In these formulae, $R^6$, $R^7$ and $R^8$ are as previously defined.

Illustrative examples of the zwitterionic surfactants suitable for use include betaines like cocodimethyl carboxymethyl betaine, cocamidopropyl betaine and laurylamidopropyl betaine. An additional zwitterionic surfactant suitable for use includes cocamidopropyl sultaine. Such surfactants are made commercially available from suppliers like Stepan Company, and it is within the scope of the invention to employ mixtures of the aforementioned surfactants. In a preferred embodiment, the zwitterionic surfactant used in this invention is cocamidopropyl betaine.

Nonionic surfactants may optionally be used in the hydratable composition and end use composition of the present invention. When used, nonionic surfactants are typically used at levels as low as 0.5, 1, 1.5 or 2% by weight and at levels as high as 6, 8, 10 or 12% by weight of the end use composition. The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic surfactant compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other nonionic surfactants include long chain tertiary amine oxides, long chain tertiary phosphine oxides, dialkyl sulphoxides, and the like.

In an embodiment of the invention, nonionic surfactants optionally used can include fatty acid/alcohol ethoxylates having the following structures a) $HOCH_2(CH_2)_s$ $(CH_2CH_2O)_v H$ or b) $HOOC(CH_2)_c(CH_2CH_2O)_d H$; where s and v are each independently an integer up to 18; and c and d are each independently an integer from 1 or greater. In an embodiment of the invention, s and v are each independently 6 to 18; c and d are each independently 1 to 30. Other options for nonionic surfactants include those having the formula $HOOC(CH_2)_i$—$CH$=$CH$—$(CH_2)_k(CH_2CH_2O)_z H$, where i, k are each independently 5 to 15; and z is 5 to 50. In another embodiment of the invention, i and k are each independently 6 to 12; and z is 15 to 35.

The nonionic may also include a sugar amide, such as a polysaccharide amide. Specifically, the surfactant may be one of the lactobionamides described in U.S. Pat. No. 5,389,279 to Au et al., entitled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

In an embodiment of the invention, cationic surfactants may optionally be used in the hydratable composition and end use composition of the present invention.

One class of optional cationic surfactants includes heterocyclic ammonium salts such as cetyl or stearyl pyridinium chloride, alkyl amidoethyl pyrrylinodium methyl sulfate, and lapyrium chloride.

Tetra alkyl ammonium salts are another useful class of cationic surfactants suitable for optional use. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides, and behenyl dimethyl ammonium chloride.

Still other types of cationic surfactants that may be used are the various ethoxylated quaternary amines and ester quats. Examples include PEG-5 stearyl ammonium lactate (e.g., Genamin KSL manufactured by Clariant), PEG-2 coco ammonium chloride, PEG-15 hydrogenated tallow ammonium chloride, PEG 15 stearyl ammonium chloride, dipalmitoyl ethyl methyl ammonium chloride, dipalmitoyl hydroxyethyl methyl sulfate, and strearyl amidopropyl dimethylamine lactate.

Even other useful cationic surfactants suitable for optional use include quaternized hydrolysates of silk, wheat, and keratin proteins, and it is within the scope of the invention to use mixtures of the aforementioned cationic surfactants.

If used, cationic surfactants will make up no more than 1.0% by weight of the hydratable composition. When present, they typically make up from 0.01 to 0.7%, and more typically, from 0.1 to 0.5% by weight of the end use composition, including all ranges subsumed therein.

In an embodiment of this invention, the end use composition of this invention will be substantially free of polymeric quaternary ammonium compounds (including salts of the same). In another embodiment, the end use composition will comprise less than 0.1% by weight polymeric quaternary ammonium compounds. In yet another embodiment, the end use composition comprises less than 0.01% by weight polymeric quaternary ammonium compounds. In even another embodiment, the hydratable composition and end use composition are free of polymeric quaternary ammonium compounds (i.e., 0.0%).

Water preferably makes up from 35 to 75% by weight of the hydratable composition, and most preferably, from 40 to 70% by weight water based on total weight of the hydratable composition, including all ranges subsumed therein.

The pH of the hydratable composition and end use composition is typically from 4.5 to 10, and preferably, from 5 to 9, and most preferably, from 5.2 to 7.5, including all ranges subsumed therein. Adjusters suitable to modify/buffer the pH may be used. Such pH adjusters include triethylamine, NaOH, KOH, $H_2SO_4$, HCl, $C_6 H_8O_7$ (i.e., citric acid) or mixtures thereof. The pH adjusters are added at amounts to yield the desired final pH.

The pH values may be assessed with commercial instrumentation such as a pH meter made commercially available from Thermo Scientific®.

Optional skin benefit agents suitable for use in this invention are limited only to the extent that they are capable of being topically applied, and suitable to dissolve in the hydratable composition and end use composition at the desired pH.

Illustrative examples of the benefit agents suitable to include in the water portion of the compositions are acids, like amino acids, such as arginine, valine or histidine. Additional water soluble benefit agents suitable for use include vitamin $B_2$, niacinamide (vitamin $B_3$), vitamin $B_6$, vitamin C, mixtures thereof or the like. Water soluble derivatives of such vitamins may also be employed. For instance, vitamin C derivatives such as ascorbyl tetraisopalmitate, magnesium ascorbyl phosphate and ascorbyl glycoside may be used alone or in combination with each other. Other water soluble benefit agents suitable for use include 4-ethyl resorcinol, extracts like sage, aloe vera, green tea, grapeseed, thyme, chamomile, yarrow, cucumber, liquorice, rosemary extract or mixtures thereof. Water soluble sunscreens like ensulizole may also be used. Total amount of optional water soluble benefit agents (including mixtures) when present in the invention may range from 0.0 to 10%, preferably from 0.001 to 8%, and most preferably, from 0.01 to 6% by weight, based on total weight of the end use composition and including all ranges subsumed therein.

It is also within the scope of the present invention to optionally include oil (i.e., non-water) soluble benefit agents. The end use composition is substantially free of oil and preferably has less than 0.15% by weight oil, and most preferably, no oil (0.0%) where oil is not meant to include any oil from a fragrance. Thus, oil soluble actives or benefit agents are solubilized in the surfactants used. The only limitation with respect to such oil soluble benefit agents are that the same are suitable to provide a benefit when topically applied. The composition has preferably less than 0.15% Petrolatum (petroleum jelly), more preferably is free from Petrolatum.

Illustrative examples of the types of oil soluble benefit agents that may optionally be used in the compositions of this invention include components like stearic acid, vitamins like Vitamin A, D, E and K (and their oil soluble derivatives), sunscreens like ethylhexylmethoxycinnamate, bisethyl hexyloxyphenol methoxyphenol triazine, 2-ethylhexyl-2-cyano-3,3-diphenyl-2-propanoic acid, drometrizole trisiloxane, 3,3,5-trimethyl cyclohexyl 2-hydroxybenzoate, 2-ethylhexyl-2-hydroxybenzoate or mixtures thereof.

Other optional oil soluble benefit agents suitable for use include resorcinols like 4-hexyl resorcinol, 4-phenylethyl resorcinol, 4-cyclopentyl resorcinol, 4-cyclohexyl resorcinol 4-isopropyl resorcinol or a mixture thereof. Also, 5-substituted resorcinols like 4-cyclohexyl-5-methylbenzene-1,3-diol, 4-isopropyl-5-methylbenzene-1,3-diol, mixtures thereof or the like may be used. The 5-substituted resorcinols, and their synthesis are described in commonly assigned U.S. Published Patent Application No. 2016/0000669A1.

Even other oil soluble actives suitable for use include omega-3 fatty acids, omega-6 fatty acids, climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, terpineol, thymol mixtures thereof or the like.

In an embodiment of the invention, the optional oil soluble benefit agent used is a retinoic acid precursor. In one embodiment of the invention, the retinoic acid precursor is retinol, retinal, retinyl propionate, retinyl palmitate, retinyl acetate or a mixture thereof. Retinyl propionate, retinyl palmitate and mixtures thereof are typically preferred.

Still another retinoic acid precursor suitable for use is hydroxyanasatil retinoate made commercially available under the name Retextra® as supplied by Molecular Design International. The same may be used in a mixture with the oil soluble actives described herein.

When optional oil soluble active is used in the compositions of the invention, it typically makes up from 0.0 to 1.5%, and preferably, from 0.001 to 1.5%, and most preferably, from 0.05 to 1.2% by weight of the end use composition. In yet another embodiment, oil makes up from 0.1 to 0.5% by weight of the total weight of the end use composition, including all ranges subsumed therein.

Preservatives can desirably be incorporated into the hydratable concentrate and end use composition to protect against the growth of potentially harmful microorganisms. Cosmetic chemists are familiar with appropriate preservatives and routinely choose them to satisfy the preservative challenge test and to provide product stability. Suitable traditional preservatives for use include hydantoin derivatives and propionate salts. Particularly preferred preservatives are iodopropynyl butyl carbamate, phenoxyethanol, 1,2-octanediol, hydroxyacetophenone, ethylhexylglycerine, hexylene glycol, methyl paraben, propyl paraben, imidazolidinyl urea, sodium dehydroacetate, dimethyl-dimethyl (DMDM) hydantoin and benzyl alcohol and mixtures thereof. Other preservatives suitable for use include sodium dehydroacetate, chlorophenesin and decylene glycol. The preservatives should be selected having regard for the use of the composition and possible incompatibilities between the preservatives and other ingredients in the emulsion. Preservatives are preferably employed in amounts ranging from 0.01% to 2.0% by weight of the total weight of the end use composition (up to 7% by weight of total hydratable composition), including all ranges subsumed therein. Also preferred is a preservative system with hydroxyacetophenone alone or in a mixture with other preservatives.

Thickening agents are optionally suitable for use in the compositions of the present invention. Particularly useful are the polysaccharides. Examples include fibers, starches, natural/synthetic gums and cellulosics. Representative of the starches are chemically modified starches such as sodium hydroxypropyl starch phosphate and aluminum starch octenylsuccinate. Tapioca starch is often preferred, as is maltodextrin. Suitable gums include xanthan, *sclerotium*, pectin, karaya, arabic, agar, guar (including Acacia senegal guar), carrageenan, alginate and combinations thereof. Suitable cellulosics include hydroxypropyl cellulose, hydroxypropyl methylcellulose, ethylcellulose, sodium carboxy methylcellulose (cellulose gum/carboxymethyl cellulose) and cellulose (e.g. cellulose microfibrils, cellulose nanocrystals or microcrystalline cellulose). Sources of cellulose microfibrils include secondary cell wall materials (e.g. wood pulp, cotton), bacterial cellulose, and primary cell wall materials. Preferably the source of primary cell wall material is selected from parenchymal tissue from fruits, roots, bulbs, tubers, seeds, leaves and combination thereof; more preferably is selected from citrus fruit, tomato fruit, peach fruit, pumpkin fruit, kiwi fruit, apple fruit, mango fruit, sugar beet, beet root, turnip, parsnip, maize, oat, wheat, peas and combinations thereof; and even more preferably is selected from citrus fruit, tomato fruit and combinations thereof. A most preferred source of primary cell wall material is parenchymal tissue from citrus fruit. Citrus fibers, such as those made available by Herbacel® as AQ Plus can also be used as source for cellulose microfibrils. The cellulose sources can be surface modified by any of the known methods including those described in Colloidal Polymer Science, Kalia et al., "Nanofibrillated cellulose: surface modification and potential applications" (2014), Vol 292, Pages 5-31.

Synthetic polymers, in addition to polymeric viscosity aids, are yet another class of effective thickening agents that can optionally be used. This category includes crosslinked polyacrylates such as the Carbomers, polyacrylamides such as Sepigel® 305 and taurate copolymers such as Simulgel® EG and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100. Calcium carbonate, fumed silica, and magnesium-aluminum-silicate may also be used.

The amounts of optional thickening agent, when used, may range from 0.001 to 5%, by weight of the compositions. Maltodextrin, xanthan gum, and carboxymethyl cellulose are the often preferred optional thickening agents.

Fragrances, fixatives, chelators (like EDTA) and exfoliants may optionally be included in the compositions of the present invention. Each of these substances may range from about 0.03 to about 5%, preferably between 0.1 and 3% by weight of the total weight of the end use composition, including all ranges subsumed therein. To the extent the exfoliants are used, those selected should be of small enough particle size so that they do not impede the performance of any packaging used to dispense the compositions of this invention.

Conventional emulsifiers having an HLB of greater than 8 may optionally be used. Illustrative examples include Tween, 40, 60, 80, polysorbate 20 and mixtures thereof. Typically, emulsifiers for water continuous systems make up from 0.3 to 2.5% by weight of the end use composition.

Conventional humectants may optionally be employed as additives in the present invention to assist in moisturizing skin when such emulsions are topically applied. These are generally polyhydric alcohol type materials. Typical poly-hydric alcohols include glycerol (i.e., glycerine or glycerin), propylene glycol, dipropylene glycol, polypropylene glycol (e.g., PPG-9), polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.0 to 35% by weight of the total weight of the compositions. Often, humectant makes up from 0.0 to 20%, and preferably, from 0.001 to 15% by weight (most preferably, from 2 to 12% by weight) of the total weight of the end use composition.

As to the end use compositions of the present invention, the same typically have from 1 to 35%, and preferably, from 2 to 30%, and most preferably, from 3 to 16% by weight total surfactant, based on total weight of the end use composition and including all ranges subsumed therein. In an embodiment of the invention, the end use composition comprises from 7 to 10% by weight total surfactant based on total weight of the end use composition and including all ranges subsumed therein.

The present invention is directed to hydratable concentrated surfactant composition that thickens and thus displays an increase in viscosity when mixed and diluted with water. In an embodiment of the invention, when the weight percent of zwitterionic surfactant to the weight percent of anionic surfactant exceeds 3:1 in the compositions, structuring agent (e.g., lauric acid) should be present at over 15% by weight of the total weight of surfactant in the compositions. Additionally, and in another embodiment of the invention, when the zwitterionic surfactant to anionic surfactant weight ratio is less than 1.5, structuring agent makes up 27% by weight or less than the total weight of surfactant in the compositions. In another embodiment, when the weight percent of zwitterionic surfactant to the weight percent of anionic surfactant exceeds 3:1 in the compositions, structuring agent (e.g., lauric acid) should be present at over 15% by weight of the total weight of surfactant in the compositions and when the zwitterionic surfactant to anionic surfactant weight ratio is less than 1.5, structuring agent makes up 27% by weight or less than the total weight of surfactant in the compositions.

When making hydratable composition of the present invention, the desired ingredients may be mixed with conventional apparatus under moderate shear and atmospheric conditions, with temperature being from 35 to 80° C. Water is added to the hydratable composition to produce the end use composition. Moderate shear such as shaking (or stirring) in a container will yield the end use composition in less than 5 minutes, preferably in less than 3 minutes, and most preferably, in less than 2 minutes. In an embodiment of the invention, end use composition is made in less than 1 minute, even preferably, less than 30 seconds.

Accordingly, the present invention relates in a further aspect to a method to prepare an end use composition, the method comprising the step of diluting a hydratable composition of the present invention with water. Preferably, the composition is diluted at a composition to water weight ratio from 1:1 to 1:10. The hydratable concentrated surfactant composition has a viscosity from 25 to 10,000 cps and upon dilution the viscosity increases resulting in an end use composition having a viscosity from 1,000 to 20,000 cps, The viscosity is measured with a Discovery HR-2 Rheometer using sand blasted plates with a 100 micron gap and a shear rate of 4-15 s-1 and at a temperature of 25° C. Preferred aspects of the end use composition have been described above.

The packaging for the compositions typically is not limited as long as hydratable composition can be hydrated and end use composition can be made upon the addition of water. In an embodiment on the invention, the hydratable composition is sold in a pouch or cartridge that is associated with and inserted in a bottle or canister. The bottle or canister is one which is filled with water and allows for the release of the hydratable composition into the same for mixing with water. Typically, the bottle or canister has a cap with a pump that opens the sachet or canister to release the hydratable composition into the water to make end use composition. Such a hydratable composition unexpectedly yields an end use composition, such as a body wash, with desirable characteristics appreciated by consumers. The packaging allows for infinite numbers of refilling to invariably reduce plastic waste in the environment.

The hydratable concentrated composition is preferably packaged in a refill packaging. Preferably, the hydratable concentrated composition is used as a refill-composition.

The Example provided is to facilitate an understanding of the invention. It is not intended to limit the scope of the claims.

EXAMPLE

All compositions represented in each Sample of the Example as set forth in the Tables were made by conventional means, and therefore, by mixing ingredients with moderate shear under atmospheric conditions at a temperature from about 35 to 75° C. The compositions (i.e., end use/diluted compositions) were made to include about 0.6% by weight of fragrance and 0.8% by weight preservative. The hydratable compositions were diluted (water to composition) at a weight ratio of 3 to 1 with the exception that the compositions of Samples 14 and 17 were a 2 to 1 water to hydratable composition dilution and the composition of Sample 16 was a 3.5 to 1 water to hydratable composition dilution. For the avoidance of doubt, "Concentrate Viscosity" means the viscosity of hydratable composition and "Dilute Viscosity" means the viscosity of the end use wash composition made, both in centipoise (cps). Water and hydratable composition were combined in a vessel and were agitated with mild shaking. In less than one (1) minute, desired wash composition was unexpectedly obtained. Tables

| Sample | CAPB | Isethionate | Taurate | Lauric Acid | NaCl | Concentrate Viscosity | Dilute Viscosity |
|---|---|---|---|---|---|---|---|
| 1 | 21.2% | 9.8% | 2.0% | 4.6% | 2.0% | 1504 | 8481 |
| 2 | 21.2% | 8.8% | 3.0% | 6.3% | 1.0% | 2580 | 11300 |
| 3 | 21.2% | 5.9% | 5.9% | 7.9% | 1.0% | 2706 | 12970 |
| 4 | 21.2% | 3.0% | 8.8% | 10.0% | 1.0% | 2926 | 5546 |
| 5 | 21.2% | 2.0% | 9.8% | 10.0% | 1.0% | 3808 | 8354 |

| Sample | CAPB | Isethionate | Methyl Isethionate | Taurate | Lauric Acid | NaCl | Concentrate Viscosity | Dilute Viscosity |
|--------|------|-------------|--------------------|---------|-------------|------|----------------------|------------------|
| 6 | 18.7% | 3.6% | 0.0% | 10.8% | 7.9% | 5.0% | 2641 | 7233 |
| 7 | 18.7% | 0.0% | 3.6% | 10.8% | 6.3% | 1.5% | 1374 | 4043 |

| Sample | CAPB | Isethionate | Taurate | Lauric Acid | NaCl | Concentrate Viscosity | Dilute Viscosity |
|--------|------|-------------|---------|-------------|------|----------------------|------------------|
| 8 | 16.5% | 13.8% | 2.8% | 11.2% | 1.0% | 114300 | 334.1 |
| 9 | 16.5% | 13.8% | 2.8% | 9.6% | 1.0% | 57540 | 734.8 |
| 10 | 16.5% | 12.4% | 4.1% | 11.2% | 1.0% | 82450 | 124 |
| 11 | 24.8% | 6.19% | 2.1% | 4.6% | 5.0% | 64680 | 19740 |

| Sample | CAPB | Isethionate | Taurate | Lauric Acid | NaCl | Mineral Oil | Concentrate Viscosity | Dilute Viscosity | Dilute Viscosity (1 week 50 degrees C.) |
|--------|------|-------------|---------|-------------|------|-------------|----------------------|------------------|------------------------------------------|
| 12 | 22.2% | 4.9% | 6.2% | 7.8% | 2.0% | 0.0% | 3926 | 14900 | 13960 |
| 13 | 22.2% | 4.9% | 6.2% | 7.8% | 2.0% | 0.3% | 3670 | 13890 | 5441 |

| Sample | Surfactant Level | CAPB | Isethionate | Taurate | Lauric Acid | NaCl | Concentrate Viscosity | Dilute Viscosity |
|--------|------------------|------|-------------|---------|-------------|------|----------------------|------------------|
| 14 | 25.6% | 17.1% | 3.8% | 4.8% | 6.0% | 6.0% | 1032 | 14330 |
| 15 | 33.0% | 21.2% | 9.8% | 2.0% | 4.6% | 3.0% | 1345 | 8514 |
| 16 | 39.7% | 24.0% | 6.1% | 9.6% | 9.4% | 2.5% | 6280 | 10030 |

| Sample | CAPB | Isethionate | Glycinate | Taurate | Lauric Acid | NaCl | Concentrate Viscosity | Dilute Viscosity |
|--------|------|-------------|-----------|---------|-------------|------|----------------------|------------------|
| 17 | 17.1% | 3.8% | 4.7% | 0.0% | 4.5% | 1.0% | 1328 | 5627 |
| 18 | 17.1% | 3.8% | 0.0% | 4.8% | 6.0% | 6.0% | 1032 | 14330 |

Tables

| Sample | CAPB | Isethionate | Taurate | Lauric Acid | NaCl | Concentrate Viscosity | Dilute Viscosity |
|--------|------|-------------|---------|-------------|------|----------------------|------------------|
| 19 | 21.2% | 9.8% | 2.0% | 4.6% | 3.0% | 1345 | 8514 |
| 20 | 16.5% | 4.1% | 12.4% | 6.3% | 12.0% | 1916 | 44.21 |
| 21 | 21.2% | 5.9% | 5.9% | 7.9% | 1.0% | 2706 | 12970 |
| 22 | 24.8% | 2.1% | 6.2% | 9.6% | 0.0% | 2803 | 10810 |

| Sample | CAPB | Isethionate | Taurate | Lauric Acid | NaCl | Concentrate Viscosity | Dilute Viscosity |
|--------|------|-------------|---------|-------------|------|----------------------|------------------|
| 23 | 21.2% | 2.0% | 9.8% | 10.0% | 1.0% | 3808 | 8354 |
| 24 | 16.5% | 4.1% | 12.4% | 6.3% | 12.0% | 1916 | 4421 |
| 25 | 21.2% | 6.0% | 5.9% | 7.9% | 1.0% | 2706 | 12970 |

-continued

| Sample | CAPB | Isethionate | Taurate | Lauric Acid | NaCl | Concentrate Viscosity | Dilute Viscosity |
|---|---|---|---|---|---|---|---|
| 26 | 21.2% | 8.8% | 3.0% | 6.3% | 1.0% | 2580 | 11300 |
| 27 | 21.2% | 9.8% | 2.0% | 4.6% | 2.0% | 1504 | 8481 |

| Sample | CAPB | Isethionate | Taurate | Lauric Acid | NaCl | Concentrate Viscosity | Dilute Viscosity |
|---|---|---|---|---|---|---|---|
| 28 | 16.5% | 12.4% | 4.1% | 4.6% | 4.0% | 1712 | 10070 |
| 29 | 18.7% | 7.2% | 7.2% | 6.3% | 0.0% | 2568 | 4755 |
| 30 | 19.8% | 9.9% | 3.3% | 6.3% | 1.0% | 2847 | 6452 |
| 31 | 21.2% | 2.0% | 9.8% | 9.6% | 1.0% | 3808 | 8354 |
| 32 | 24.8% | 2.1% | 6.2% | 9.6% | 0.0% | 2803 | 10810 |

| Sample | CAPB | Isethionate | Taurate | Lauric Acid | NaCl | Versathix | Concentrate Viscosity | Dilute Viscosity |
|---|---|---|---|---|---|---|---|---|
| 33 | 20.5% | 10.4% | 2.1% | 5.5% | 0.0% | 0.2% | 1958 | 11560 |
| 34 | 18.7% | 3.6% | 10.8% | 6.3% | 5.0% | 0.2% | 1540 | 8455 |

CAPB—cocamidopropyl betaine
Isethionate- Sodium cocoyl isethionate;
methyl isethionate- sodium methyl lauroyl isethionate
Taurate- sodium methyl lauroyl taurate
Versathix- PEG 150 pentaerythritol tetrastearate As can be seen from the data provided, the hydratable compositions made according to this invention where prepared in less than one (1) minute of agitation and they surprisingly thickened (increased in viscosity) when combined with water.

The invention claimed is:

1. A method for making an end use composition comprising the steps of combining:
   a) a hydratable concentrated surfactant composition having a viscosity from 250 to 7,500 cps wherein the composition comprises:
      i) an anionic surfactant comprising acyl isethionate and acyl taurate the acyl isethionate making up from 15 to 85% by weight of the total weight of anionic surfactant;
      ii) an amphoteric and/or zwitterionic surfactant;
      iii) a $C_6$-$C_{14}$ acid or alcohol;
      iv) humectant and fragrance;
      v) from 30 to 85% by weight water; and
   b) water; and
   c) producing the end use composition
wherein the hydratable concentrated surfactant composition and water are combined at a weight ratio from 1:3 to 1:6 to produce the end use composition, the end use composition having a viscosity from 3,000 to 15,000 cps and less than 3.0% by weight sulfate and further wherein the hydratable concentrated surfactant composition further comprises an inorganic salt, a polymeric viscosity aid, lauric acid or a mixture thereof.

2. The method according to claim 1 wherein the hydratable concentrated surfactant composition further comprises a vitamin.

3. The method according to claim 1 wherein the anionic surfactant comprising an acyl isethionate and acyl taurate further comprises an additional anionic surfactant.

4. The method according to claim 3 wherein the additional anionic surfactant is an acyl glycinate or a mixture thereof.

5. The method according to claim 1 wherein 15 to 80% by weight of the anionic surfactant is acyl isethionate and the polymeric viscosity aid is present and comprises PEG 150 pentaerythritol tetrastearate.

6. The method according to claim 1 wherein the acyl taurate comprises sodium methyl cocoyl taurate, sodium methyl lauroyl taurate or a mixture therefore and the acyl isethionate comprises sodium lauroyl isenthionate, sodium cocyl isethionate or a mixture thereof.

7. The method according to claim 1 wherein the zwitterionic surfactant is cocamidopropyl betaine and the acid is present and is lauric acid and the hydratable concentrated surfactant composition does comprise 0.01 to 0.8% by weight of the polymeric viscosity aid.

8. The method according to claim 1 wherein the anionic surfactant in the hydratable concentrated surfactant composition and end use composition is acyl isethionate and acyl taurate.

9. The method according to claim 8 wherein the anionic surfactant makes up from 0.8 to 20% by weight of the hydratable concentrated surfactant composition.

* * * * *